United States Patent
Gerber et al.

(10) Patent No.: US 7,734,353 B2
(45) Date of Patent: Jun. 8, 2010

(54) CONTROLLING TEMPERATURE DURING RECHARGE FOR TREATMENT OF INFECTION OR OTHER CONDITIONS

(75) Inventors: Martin T. Gerber, Maple Grove, MN (US); John C. Rondoni, Plymouth, MN (US)

(73) Assignee: Medtronic Inc., Minneapolis, MN (US)

(*) Notice: Subject to any disclaimer, the term of this patent is extended or adjusted under 35 U.S.C. 154(b) by 618 days.

(21) Appl. No.: 11/737,179

(22) Filed: Apr. 19, 2007

(65) Prior Publication Data

US 2009/0005770 A1    Jan. 1, 2009

(51) Int. Cl.
*A61N 1/08* (2006.01)
(52) U.S. Cl. .............. 607/61; 607/29; 607/34; 607/96; 607/102; 607/113
(58) Field of Classification Search ............ 607/61, 607/33, 34
See application file for complete search history.

(56) References Cited

U.S. PATENT DOCUMENTS

| | | | | |
|---|---|---|---|---|
| 3,170,465 | A | * | 2/1965 | Henney et al. ............ 607/113 |
| 3,867,950 | A | * | 2/1975 | Fischell ................. 607/33 |
| 4,082,097 | A | | 4/1978 | Mann |
| 5,029,582 | A | | 7/1991 | Lekholm |
| 5,181,905 | A | | 1/1993 | Flam |
| 5,476,485 | A | | 12/1995 | Weinberg |
| 5,546,955 | A | | 8/1996 | Wilk |
| 5,733,313 | A | * | 3/1998 | Barreras et al. ............ 607/33 |
| 5,807,270 | A | | 9/1998 | Williams |
| 5,820,263 | A | | 10/1998 | Ciobanu |
| 6,016,447 | A | | 1/2000 | Juran |
| 6,113,539 | A | | 9/2000 | Ridenour |
| 6,135,968 | A | | 10/2000 | Brounstein |
| 6,248,080 | B1 | | 6/2001 | Miesel et al. |
| 6,282,444 | B1 | | 8/2001 | Kroll |
| 6,356,774 | B1 | | 3/2002 | Bernstein |
| 6,558,351 | B1 | | 5/2003 | Steil |
| 6,901,296 | B1 | | 5/2005 | Whitehurst |
| 6,963,772 | B2 | | 11/2005 | Bloom |

(Continued)

FOREIGN PATENT DOCUMENTS

DE    10150343 A1    4/2003

(Continued)

OTHER PUBLICATIONS

PCT International Search Report dated Nov. 19, 2007.

(Continued)

*Primary Examiner*—Kennedy J Schaetzle
(74) *Attorney, Agent, or Firm*—Campbell Nelson Whipps LLC

(57) ABSTRACT

Methods include determining whether an infection is in proximity to an implanted rechargeable medical device. If an infection is determined to be present, the recharge process is allowed to sufficiently heat the device to facilitate clearing of the infection. Additional methods include monitoring temperature in proximity to an implantable rechargeable device in connection with recharging the device. If the monitored temperature falls outside a desired range, one or more parameters associated with recharge energy are modified to cause the temperature to reside within the desired range. The desired temperature range, may be a range that can facilitate treatment of a condition in proximity to the implanted device without causing undesired damage to the patient's tissue surrounding the implanted device.

21 Claims, 10 Drawing Sheets

U.S. PATENT DOCUMENTS

| | | |
|---|---|---|
| 6,970,741 B1 | 11/2005 | Whitehurst |
| 7,049,824 B2 | 5/2006 | Shabino |
| 7,171,252 B1 | 1/2007 | Scarantino |
| 2002/0042596 A1 | 4/2002 | Hartlaub |
| 2003/0032892 A1 | 2/2003 | Erlach |
| 2003/0194752 A1 | 10/2003 | Anderson |
| 2003/0199783 A1 | 10/2003 | Bloom |
| 2003/0216677 A1 | 11/2003 | Pan |
| 2004/0066313 A1 | 4/2004 | Ong |
| 2004/0236192 A1 | 11/2004 | Necola Shehada |
| 2005/0012610 A1 | 1/2005 | Liao |
| 2005/0090761 A1 | 4/2005 | Carney |
| 2005/0096584 A1 | 5/2005 | Ferek-Petric |
| 2005/0171580 A1 | 8/2005 | MacDonald |
| 2006/0047218 A1 | 3/2006 | Bloom |
| 2006/0062852 A1 | 3/2006 | Holmes |
| 2006/0079793 A1 | 4/2006 | Mann |
| 2006/0149331 A1 | 7/2006 | Mann |
| 2006/0224088 A1 | 10/2006 | Roche |
| 2006/0271108 A1 | 11/2006 | Libbus |
| 2008/0064980 A1 | 3/2008 | Lee |

FOREIGN PATENT DOCUMENTS

| | | |
|---|---|---|
| GB | 2 405 203 | 2/2005 |
| WO | WO 02/068049 | 9/2002 |
| WO | WO 2005/000091 | 1/2005 |
| WO | WO 2005/000160 | 1/2005 |
| WO | WO 2006/013585 | 2/2006 |
| WO | WO 2006/048554 | 5/2006 |
| WO | WO 2007/028035 | 3/2007 |

OTHER PUBLICATIONS

U.S. Appl. No. 60/825,101, filed Sep. 2006, Lee.
PCT International Search Report dated Oct. 10, 2007.
PCT International Search Report dated Dec. 5, 2007.
U.S. Appl. No. 11/737,180, filed Apr. 19, 2007, Gerber.
U.S. Appl. No. 11/737,173, filed Apr. 19, 2007, Gerber.
U.S. Appl. No. 11/737,176, filed Apr. 19, 2007, Gerber.
U.S. Appl. No. 11/737,181, filed Apr. 19, 2007, Gerber.
U.S. Appl. No. 11/737,171, filed Apr. 19, 2007, Gerber.
U.S. Appl. No. 11/737,170, filed Apr. 19, 2007, Gerber.
U.S. Appl. No. 11/737,169, filed Apr. 19, 2007, Gerber.
Robicsek, F., et al., The value of thermography in the early diagnosis of postoperative sternal wound infections. Thoracic & Cardiovascular Surgeon, 1984, 32(4): p. 260-5.
Saxena, A.K., et al., Thermography of Clostridium perfringens infection in childhood. Pediatric Surgery International, 1999. 15(1): p. 75-6.
Waterman, N.G., L. Goldberg, and T. Appel, Tissue temperatures in localized pyogenic infections. American Journal of Surgery, 1969. 118(1): p. 31-5.

* cited by examiner

CONTROLLING TEMPERATURE DURING RECHARGE FOR TREATMENT OF INFECTION OR OTHER CONDITIONS

FIELD

This disclosure relates, inter alia, to implantable rechargeable medical devices. More particularly, it relates to systems, devices and methods for controlling temperature during recharge to aid in treatment of a condition, such as infection, in proximity to medical devices implanted in patients.

BACKGROUND

The medical device industry produces a wide variety of electronic and mechanical devices for treating patient medical conditions. For some medical conditions, medical devices provide the best, and sometimes the only, therapy to restore an individual to a more healthful condition and a fuller life. Examples of implantable medical devices include neurostimulators, infusion devices, pacemakers, defibrillators, diagnostic recorders, and cochlear implants. While such devices may vary in their mechanisms of therapeutic or diagnostic action or their therapeutic or diagnostic target, they do share common concerns or design issues.

For example, it is desirable to minimize the rate of infection associated with implantation of medical devices; as such infections are a serious health and economic concern. Today, infections associated with implanted medical devices are not very common due to care and precautions taken during surgical implantation of the devices. However, when infection associated with an implanted medical device does occur, explanting the device is often the only appropriate course of action.

In addition, it is desirable to design such devices such that they fit comfortably within a patient and provide therapy for an extended period of time. However, some medical devices provide therapies with significant power demands, placing limits on how small the size of power supply may be. To reduce the size of such implantable medical devices and extend their therapeutic life, rechargeable power supplies, which can be smaller than their non-rechargeable counterparts, may be employed. Recharging of such devices typically includes applying to a recharge coil of the implanted device a transcutaneous recharge signal produced by a primary coil. However, the recharge process causes heating of the implanted device and surrounding patient tissue, particularly in proximity to the secondary recharge coil. Excessive heating may result in damage to the patient tissue. Accordingly, the amount of energy applied is controlled over time to minimize heating.

While it may be desirable to minimize the amount of heat allowed to generate during a recharge process to avoid damage to tissue of the patient, it may be desirable to allow for heating of the device when an infection is present to improve clearance of the infection.

SUMMARY

The present disclosure describes, inter alia, systems, devices and methods that can be used to allow for increased heating of the implanted device during recharge to facilitate in the treatment of a condition, such as infection, in proximity to the implanted device.

In various embodiments, a method is described. The method includes determining whether an infection is present in proximity to an implanted rechargeable medical device and transmitting energy from an external source to the implanted device. The transmitted energy is capable of recharging the implanted device. If it is determined that no infection is present in proximity to the implanted device, the transmitted energy has a first parameter profile. If it is determined that an infection is present in proximity to the implanted device, the energy transmitted has a second parameter profile. The second energy parameter profile, relative to the first energy parameter profile, is configured to cause increased heating of the implanted device during the transmission of energy.

In various embodiments, a method is described. The method includes transmitting energy from an external source to an implanted rechargeable device. The energy is capable of heating a surface of the implanted device and is capable of recharging the implanted device. The method further includes monitoring temperature in proximity to the device during the transmission of the energy and determining whether the monitored temperature is above or below a desired temperature range. If it is determined that the monitored temperature is above or below the desired temperature range, one or more parameters of the transmitted energy are modified. The modified parameters are configured to cause the monitored temperature to reside within the desired temperature range. The method further includes determining whether the implanted device is recharged to a desired level and determining whether the device has been heated a desired amount. If it is determined that the device is recharged to the desired level and if the device has been heated the desired amount, the transmission of energy is stopped.

By providing devices, systems and methods that determine whether an infection is present in proximity to an implanted rechargeable medical device and allow for increased heating of the implanted device during recharge, such systems, devices and methods can facilitate clearance of the infection. In addition, systems, methods, and devices that allow for increased heating during recharge can be used to treat other conditions that may be associated with the implantation of the device, including pain or discomfort, edema, seromas and hematomas. Further, the use of energy to recharge and generate therapeutic heat reduces the number of procedures to which a patient is subjected. The use of existing recharge equipment can serve to reduce costs associated with a patient receiving such heat therapy; e.g., there in no need to purchase additional equipment. These and other advantages will be readily understood from the following detailed descriptions when read in conjunction with the accompanying drawings.

Figure 1:
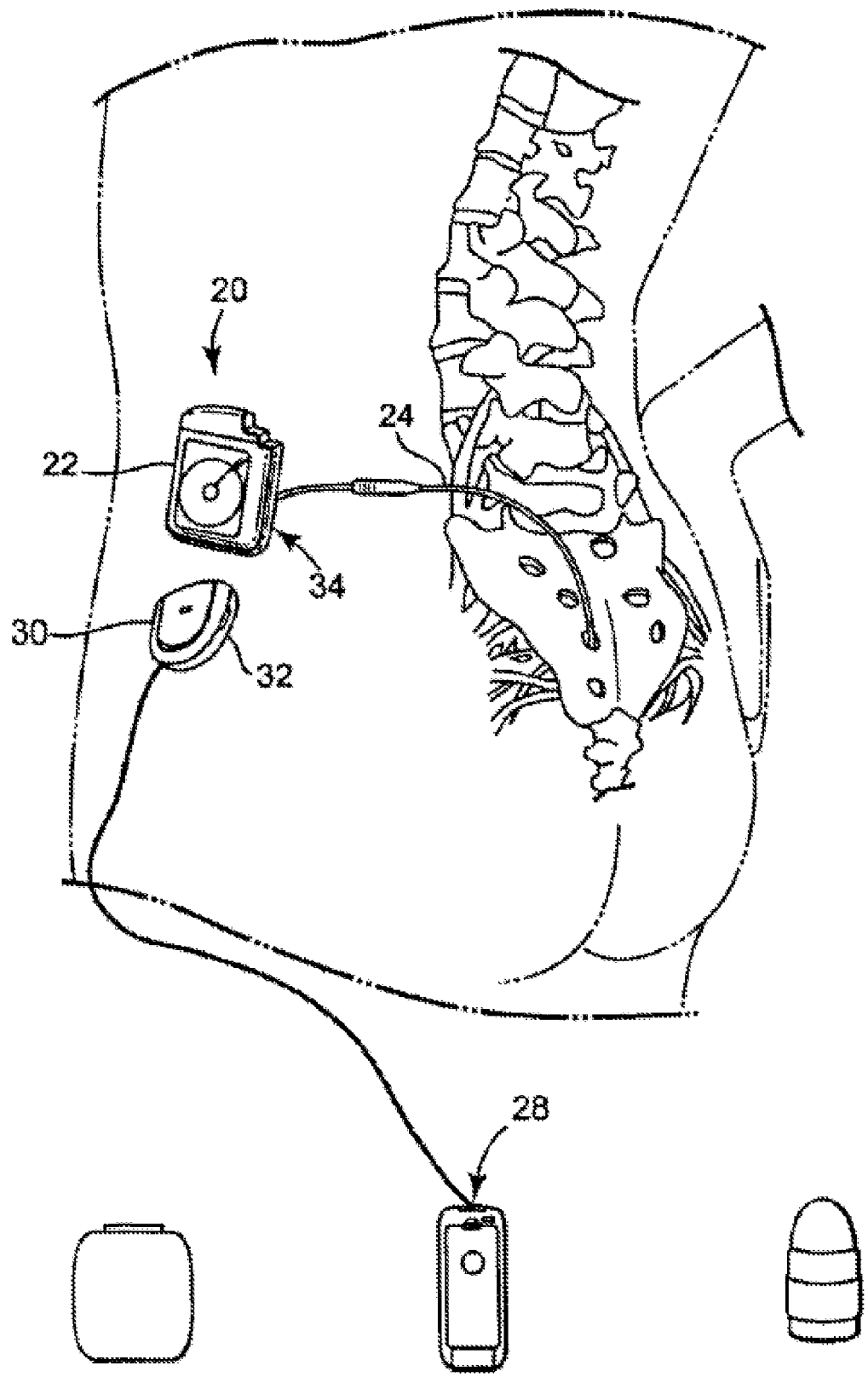
FIG. 1 is a diagrammatic representation of a perspective view of an environment of a rechargeable system including a rechargeable medical device implanted in a patient.

The drawings are not necessarily to scale. Like numbers used in the figures refer to like components, steps and the like. However, it will be understood that the use of a number to refer to a component in a given figure is not intended to limit the component in another figure labeled with the same number.

DETAILED DESCRIPTION

In the following detailed description, reference is made to the accompanying drawings that form a part hereof, and in which are shown by way of illustration several specific embodiments of devices, systems and methods. It is to be understood that other embodiments are contemplated and may be made without departing from the scope or spirit of the present invention. The following detailed description, therefore, is not to be taken in a limiting sense.

All scientific and technical terms used herein have meanings commonly used in the art unless otherwise specified. The definitions provided herein are to facilitate understanding of certain terms used frequently herein and are not meant to limit the scope of the present disclosure.

As used in this specification and the appended claims, the singular forms "a", "an", and "the" encompass embodiments having plural referents, unless the content clearly dictates otherwise. As used in this specification and the appended claims, the term "or" is generally employed in its sense including "and/or" unless the content clearly dictates otherwise.

Unless otherwise indicated, all numbers expressing feature sizes, amounts, and physical properties used in the specification and claims are to be understood as being modified in all instances by the term "about." Accordingly, unless indicated to the contrary, the numerical parameters set forth in the foregoing specification and attached claims are approximations that can vary depending upon the desired properties sought to be obtained by those skilled in the art utilizing the teachings disclosed herein.

The recitation of numerical ranges by endpoints includes all numbers subsumed within that range (e.g. 1 to 5 includes 1, 1.5, 2, 2.75, 3, 3.80, 4, and 5) and any range within that range.

The present disclosure describes, inter alia, systems, devices and methods that can be used to allow for increased heating of an implanted device during recharge to facilitate in treatment of a condition, such as infection, in proximity to the implanted device. While not intending to be bound by theory, it believed that heat generated in proximity to the implanted device will cause increased circulation and associated healing of various conditions that may be associated with the implanted device. Increased circulation may result in increased delivery of therapeutic agents, if taken, to aid in treatment of the condition. In some embodiments, heat may be used to ablate tissue, such as infected tissue, to facilitate treatment of the condition.

In various embodiments, methods, systems and devices are described in which it is determined whether an infection is in proximity to an implanted rechargeable medical device. If an infection is determined to be present, the recharge process is allowed to sufficiently heat the device to facilitate clearing of the infection.

In various embodiments, methods, systems and devices are described in which temperature in proximity of an implantable rechargeable device is monitored in connection with recharging the device. If the monitored temperature falls outside a desired range, one or more parameters associated with recharge energy are modified to cause the temperature to reside within the desired range. The desired temperature range, in various embodiments, is a range that can facilitate treatment of a condition in proximity to the implanted device without causing undesired damage to the patient's tissue surrounding the implanted device.

Referring to FIG. 1, the general environment of an embodiment of a rechargeable implantable medical device 20 is shown. An implantable electrical signal generator 22 is shown in FIG. 1, but other embodiments such as drug delivery pumps, pacemakers, defibrillators, diagnostic recorders, cochlear implants, and the like are also applicable. Implantable medical devices 20 are often implanted subcutaneously approximately one centimeter below the surface of the skin with an associated therapy delivery element, such as an electrical lead 24 or catheter, extending to one or more therapy sites. Rechargeable implantable medical device 20 is recharged with a recharging device 28 such as a patient charger or programmer that also has a charging capability.

Recharging an implantable medical device 20 generally begins with placing a recharging head 30 containing a primary recharging coil 32 against the patient's skin near the proximal side of the medical device 20. Some rechargers 28 have an antenna locator that indicates when recharge head 30 is aligned closely enough with implanted medical device 20 for adequate inductive charge coupling. The recharge power transfer signal is typically a frequency that will penetrate transcutaneous to the location of implanted medical device 20 such as a frequency in the range from 5.0 KHz to 100 KHz. The power transfer signal is converted by implantable medical device 20 into regulated DC power that is used to charge a rechargeable power source 34. Telemetry can also be conducted between the recharger 28 and the implanted medical device 20 during recharging. Telemetry can be used to aid in aligning recharger 28 with the implanted medical device 20, and telemetry can be used to manage the recharging process.

Telemetry is typically conducted at a frequency in the range from 150 KHz to 200 KHz using a medical device telemetry protocol, but may also include Bluetooth®, 802.11, and Medical Implant Communication Service (MICS) frequency band communication. For telemetry, the recharger 28 and implanted medical device 20 typically have a separate telemetry coil. Although, the recharging coil can be multiplexed to also serve as a telemetry coil.

Figure 2:
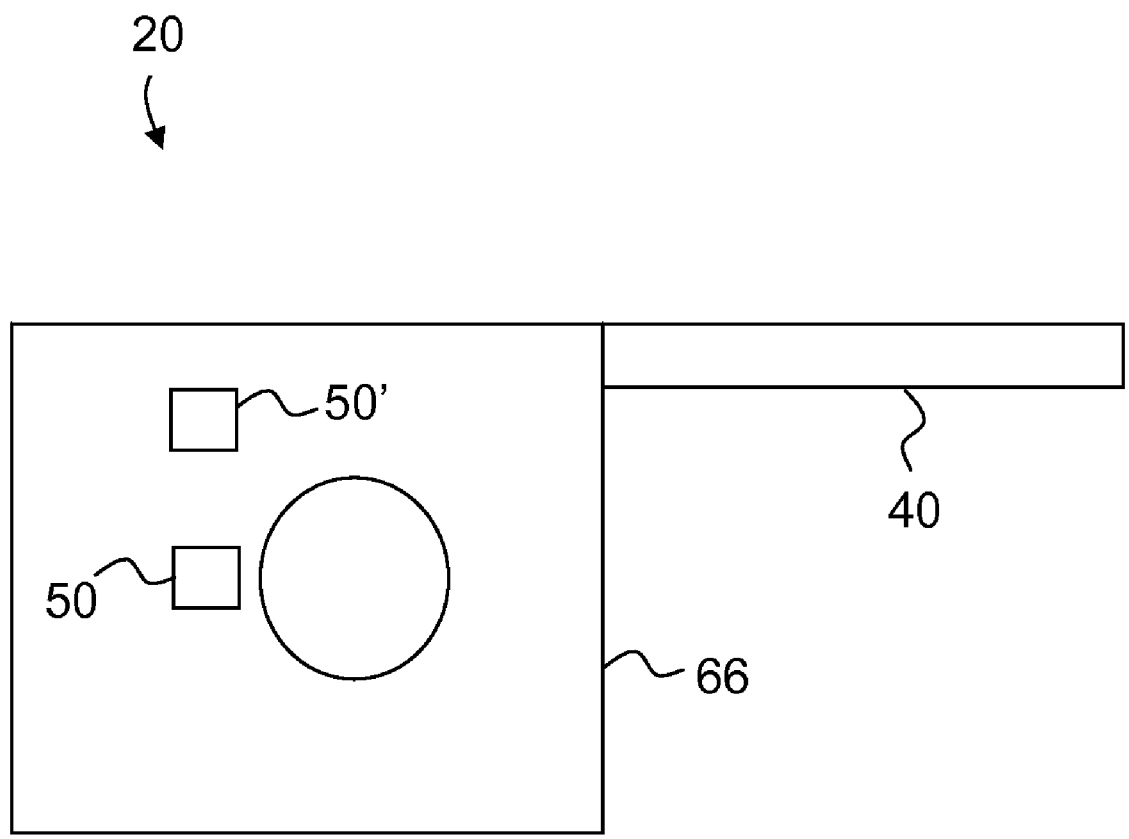
FIG. 2 is a schematic diagram of a side view of a representative implantable medical system.

Referring to FIG. 2, a rechargeable implantable medical device 20 with an associated therapy delivery element 40 is shown. Therapy delivery element 40 may be a lead 24, catheter, or the like. As shown in FIG. 2, one or more sensors 50, 50' may be associated with rechargeable implantable medical device. Sensors 50, 50' may be located in proximity to device 20, e.g. disposed on, in, or near housing 66 of device 20. Sensors 50, 50' may be used to monitor temperature, an indicator of infection, etc.

In general, sensor 50, 50' may be any device capable of detecting and transmitting information to device 20. If housing 66 is hermetically sealed, feedthroughs may be used to provide electrical connectivity through housing 66 while maintaining the hermetic seal. While not shown, it will be understood that one or more sensor capable of detecting an indicator of infection may be located on, in, or about accessory therapeutic element 40. In various embodiments, sensor 50, 50' is capable of detecting information regarding an indicator of infection or is capable of detecting and transmitting information that may be useful in determining whether an indicator of infection may actually be indicative of infection. Additional information regarding such sensing and use of such information in systems including implantable medical devices is provided in (i) U.S. patent application Ser. No. 11/737,180, entitled "INDICATOR METRICS FOR INFECTION MONITORING", filed on even date herewith, naming Martin Gerber and John Rondoni as inventors, now U.S. Pat. No. 7,611,483; and (ii) U.S. patent application Ser. No. 11/737,181, entitled "Multi-Parameter Infection Monitoring", filed on even date herewith, naming Martin Gerber and John Rondoni as inventors, now U.S. Pat. No. 7,611,483, which applications are hereby incorporated herein by reference in their respective entireties to the extent they do not conflict with the disclosure presented herein. Examples of physical or chemical stimuli that may serve as indicators of infection are temperature, impedance, pH, and biological markers of infection. Examples of parameters that may be provide information useful for determining whether an indicator of infection may actually be indicative of infection include parameters indicative of patient activity.

In addition to being monitored as an indicator of infection, temperature may be monitored in connection with recharging device 20 to determine whether temperature is in a desired range. If temperature is not within the desired range, one or more parameters associated with recharge energy, such as current amplitude or frequency, may be modified to encourage temperature in proximity to the surface of device 20 to return to the desired range. Any suitable sensor 50, 50' capable of detecting temperature or changes in temperature may be employed. For example, temperature sensor 50, 50' may include a thermocouple, a thermistor, a junction-based thermal sensor, a thermopile, a fiber optic detector, an acoustic temperature sensor, a quartz or other resonant temperature sensor, a thermo-mechanical temperature sensor, a thin film resistive element, or the like.

Figure 3:
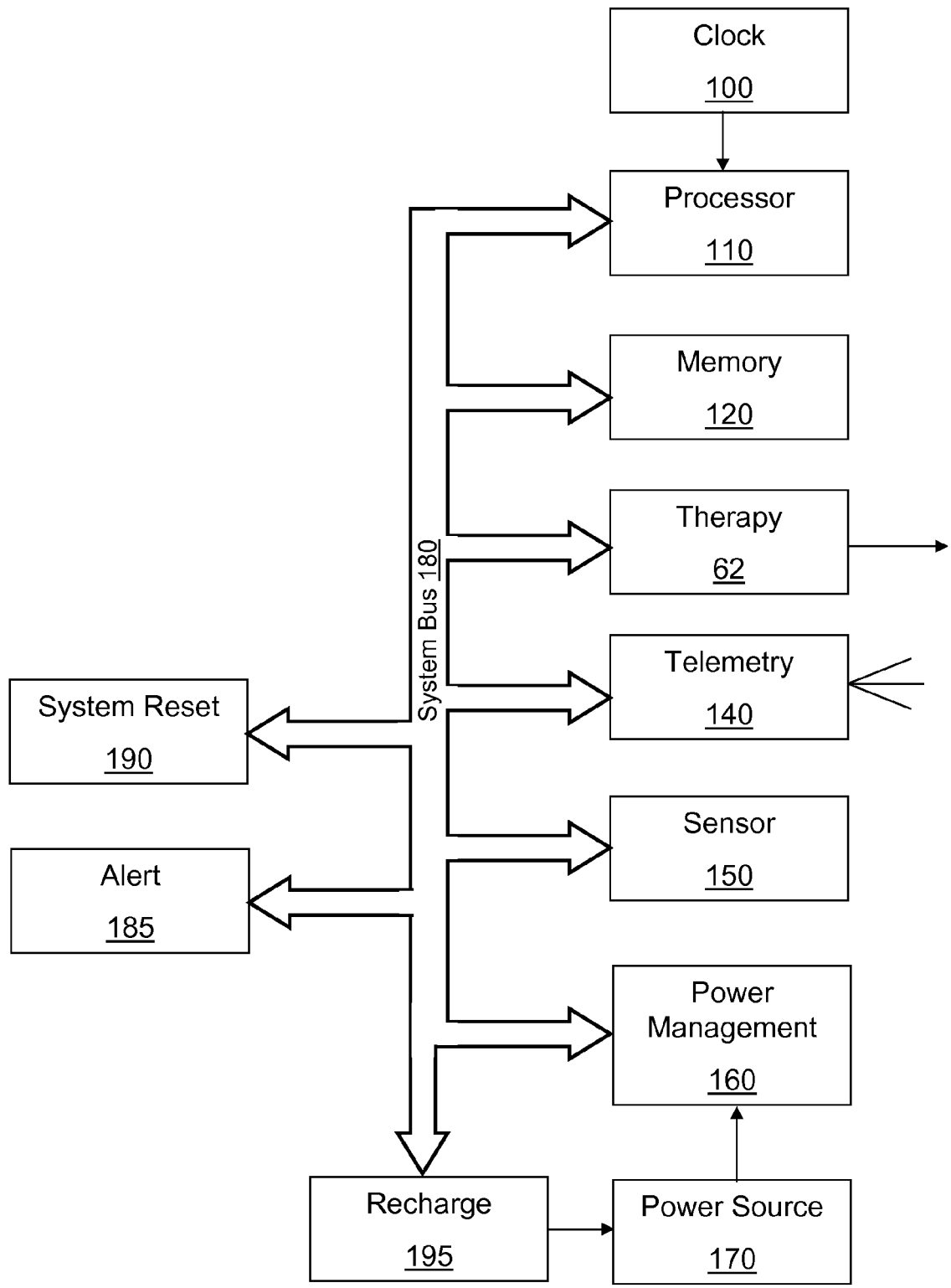
FIG. 3 is a schematic block diagram of representative components of a representative rechargeable implantable medical device.

Referring to FIG. 3, some representative electronic components of a rechargeable implantable medical device 20 according to various embodiments are shown in block form. The various components may be contained in, carried on or connected to housing 66. Implantable rechargeable medical device 20 as depicted in the embodiment shown in FIG. 3 includes a clock 100, a processor 110, a memory 120, a therapy output or delivery component 62, a telemetry component 140, a sensor 150, a power management module 160, a power source 58, an alert module 185, a system reset module 190 and a recharge module 195. Other components of implantable medical device 20 can include, e.g., a diagnostics module (not shown). All components except the power source 58 can be configured on one or more Application Specific Integrated Circuits (ASICs) or may be one or more discrete components, or a combination of both. Also, all components, except the clock and power source may be connected to bi-directional data bus 180 that is non-multiplexed with separate address and data lines.

Processor 110 may be synchronous and typically operates on low power, such as Motorola 68HC11 synthesized core operating with a compatible instruction set. Clock 100 counts the number of seconds since a fixed date for date/time stamping of events and may be used for therapy control. Memory 120 includes memory sufficient for operation of device 1, such as volatile Random Access Memory (RAM) for example static RAM, nonvolatile Read Only Memory (ROM), Electrically Erasable Programmable Read Only Memory (EEPROM) for example Flash EEPROM, and register arrays configured on ASICs. Direct Memory Access (DMA) is available to selected modules such as telemetry module 6 or sensor module 150, so that the selected modules can request control of data bus 180 and write data directly to memory 120 bypassing processor 110. System Reset 190 controls operation of ASICs and modules during power-up of device 20, so ASICs and modules registers can be loaded and brought on-line in a stable condition.

Telemetry 140 module or other wireless module provides for communication between implantable device 20 and external device 40 such as a programmer. Communication may be bi-directional. Telemetry module 140 generally includes a telemetry antenna, a receiver, a transmitter, and a telemetry processor. In some embodiments, a recharge coil may be co-opted for use as a telemetry antenna. Telemetry modules are generally known in the art and are further detailed in U.S. Pat. No. 5,752,977, entitled "Efficient High Data Rate Telemetry Format For Implanted Medical Device" issued to Grevious et al. (May 19, 1998), which is incorporate herein by reference in its entirety to the extent that it does not conflict with the disclosure presented herein. While module 140 is referred to herein as "telemetry" module, it will be understood that other forms of wireless communication may readily be substituted where appropriate for telemetry. Examples of forms of wireless communication include Bluetooth®, 802.11, and Medical Implant Communication Service (MICS) frequency band communication.

Therapy module 62 refers to components for carrying out the delivery or generation of therapeutic output to be delivered to a patient from active device 20. One of skill in the art will appreciate that the components may vary on a device-by-device basis and a therapy-by-therapy basis. For example, therapy module 62 may contain an oscillator if device 20 is an electrical signal generator and may contain a pumping mechanism if device 20 is an infusion device.

Sensor module 150 includes circuitry associated with one or more sensors 50, 50' and may include other components for transmitting sensed information from sensor 50, 50' to, e.g., processor 110 or memory 120. Sensor module 150 or other components of device 20 may include one or more analog to digital converters to convert analog signals generated by sensor 50 into digital signals usable by processor 110, as well as suitable filter and amplifier circuitry.

Alert module 185 may issue an alert, e.g. an audible alert or tactile alert, such as a vibration. An alert may be issued if information indicative of an infection is detected, if a potential adverse situation, e.g. excessive heating of device 20, is detected, if a power source is nearing depletion, or the like. The alert will serve to prompt the patient to seek medical attention.

Figure 4A:
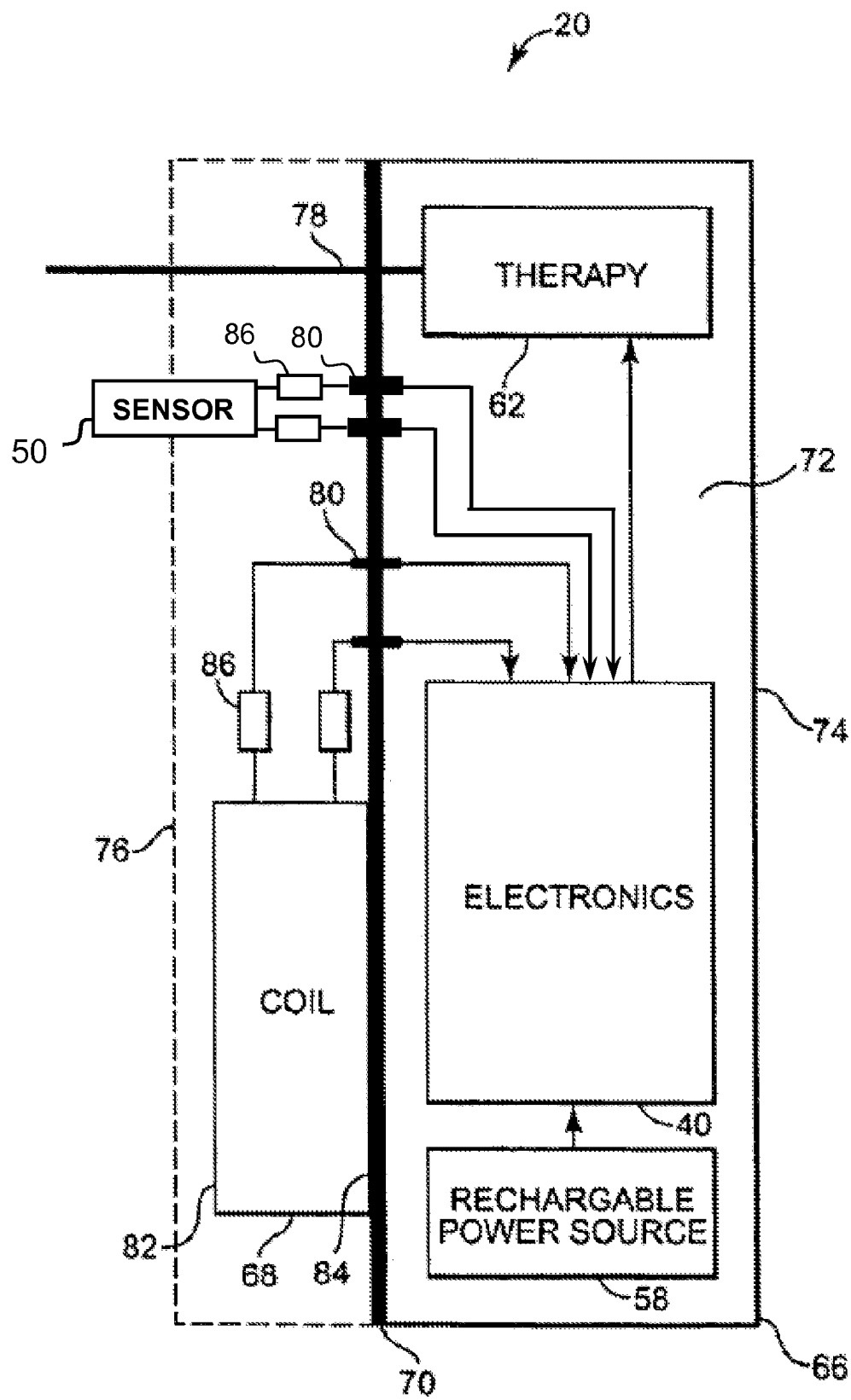
FIGS. 4A-C are schematic block diagrams of rechargeable implantable medical devices with recharging coils and optional sensors
Figure 4B:
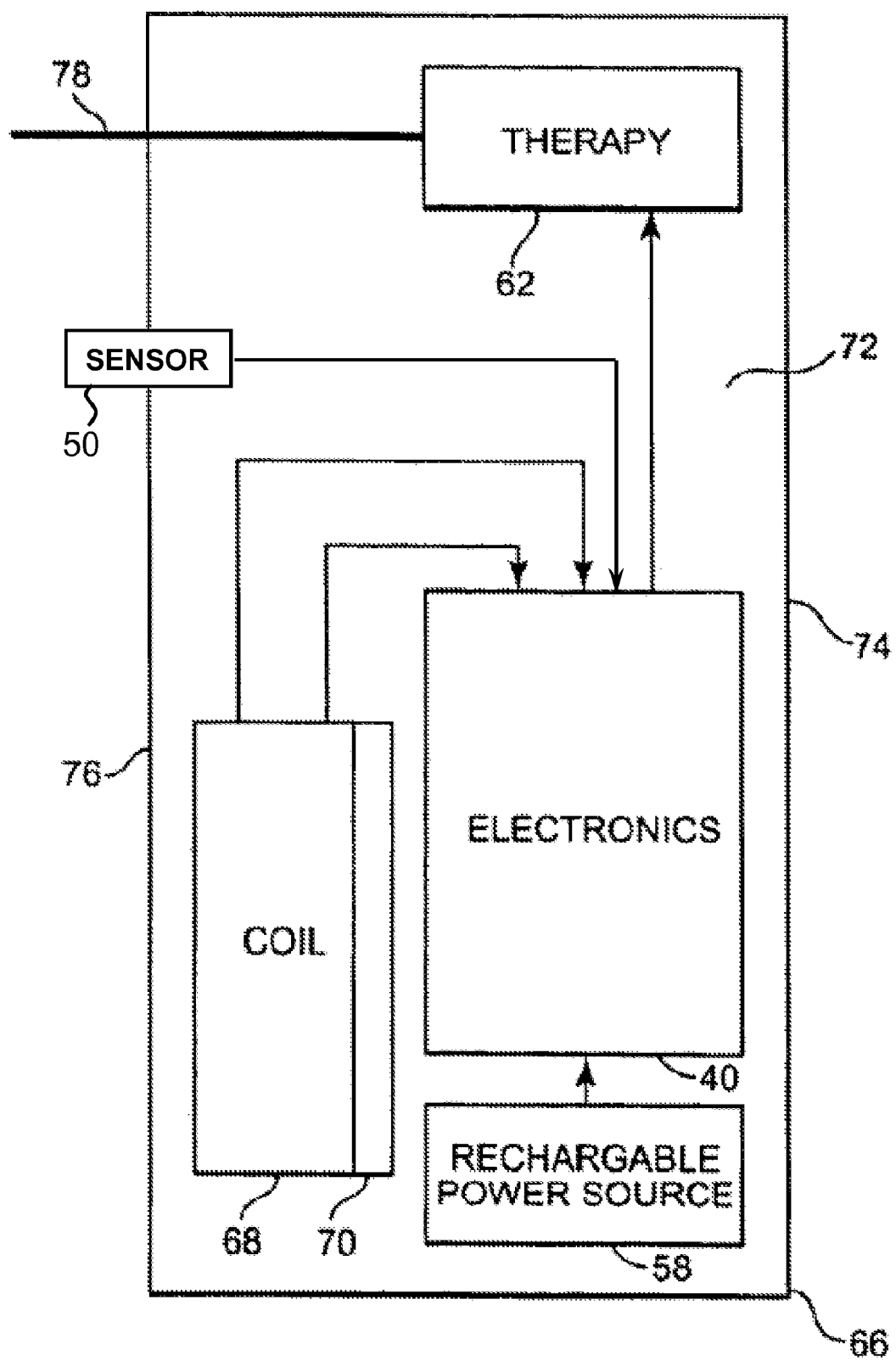
Figure 4C:
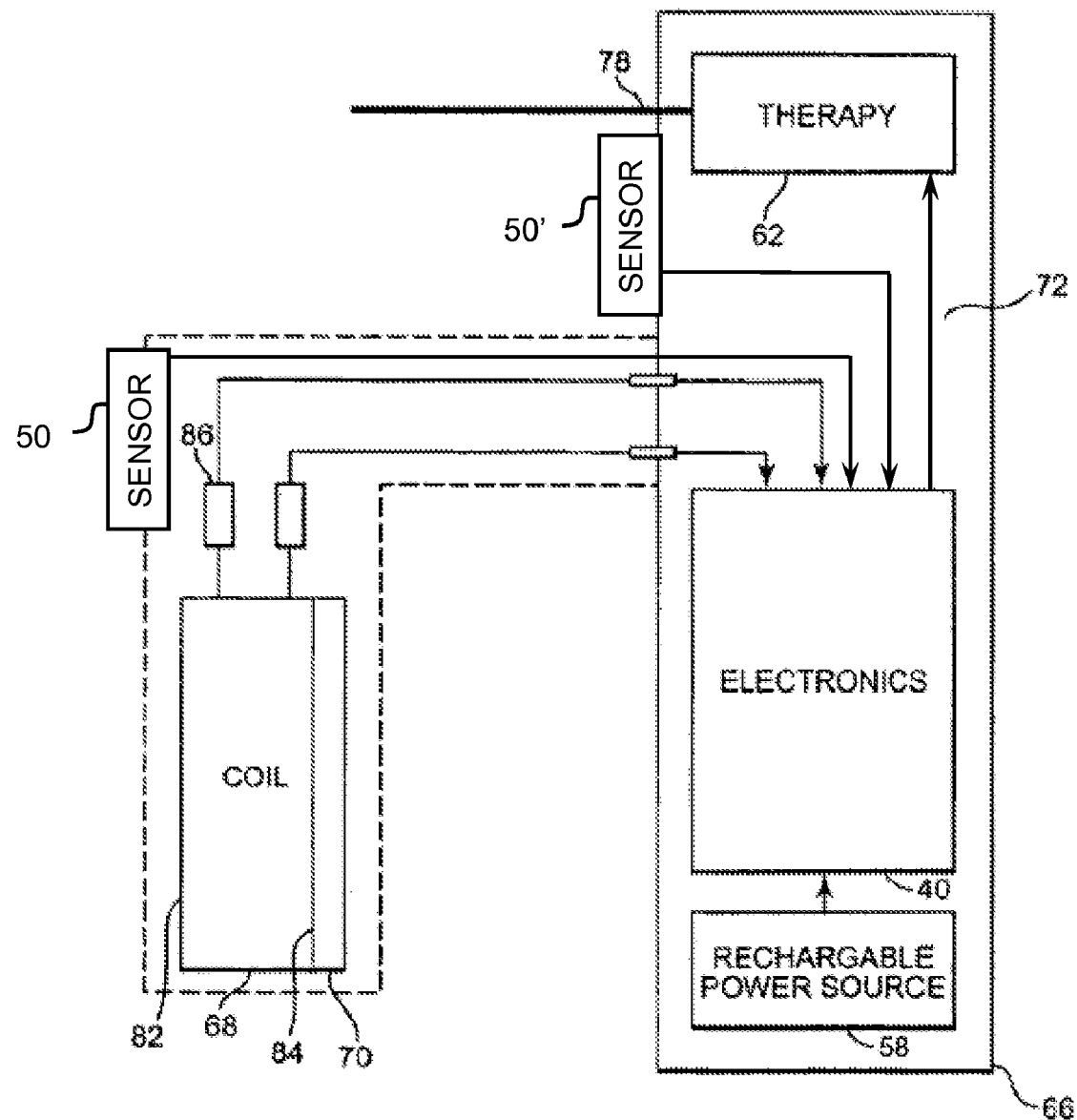

Referring to FIGS. 4A-C, schematic diagrams of implantable medical devices 20 are shown in block form. Implantable medical device 20 with external recharging coil magnetic shield includes a housing 66, electronics 40, a rechargeable power source 58, a secondary recharging coil 68, and a magnetic shield 70. Housing 66 has an interior cavity 72, an exterior surface 74, a proximal face 76, a therapy connection 78, and a recharge feedthrough 80. The therapy connection 78 can be any type of therapy connection 78 such as a stimulation feedthrough, a drug infusion port, or a physiological sensor. There can also be more than one therapy connection 78 and a combination of different types of therapy connections 78. Housing 66 is hermetically sealed and manufactured from a biocompatible material such as titanium, epoxy, ceramic, and the like. Housing 66 contains electronics 40.

Electronics 40 are carried in the housing interior cavity 72 and configured to perform a medical therapy. Electronics 40 are electrically connected to both a therapy module therapy connection 78 and recharge feedthrough 80. Rechargeable power source 58 is carried in the housing interior cavity 72 and coupled to electronics 40. Rechargeable power source 58 can be a physical power source such as a spring, an electrical power source such as a capacitor, or a chemical power source such as a battery. The battery can be a hermetically sealed rechargeable battery such as a lithium ion (Li+) battery or the like. Electronics 40 are coupled to secondary recharging coil 68.

Secondary recharging coil 68 is coupled to electronics 40 and can also be coupled to rechargeable power source 58 in addition to electronics 40. In various embodiments, the secondary recharging coil 68 can be located on housing proximal face 76, inside housing 66, and remotely away from housing 66. The secondary recharging coil 68 has a proximal side 82 implanted toward a patient's skin and a distal side 84 implanted toward a patient's internal organs. Secondary recharging coil 68 is manufactured from a material with electromagnetic properties such as copper wire, copper magnet wire, copper litz, woven wire, gold alloy or the like. Secondary recharging coil 68 can be manufactured from a wide variety of sizes such as wire diameters in the range from about 0.016 cm (34 AWG, American Wire Gauge) to about 00.40 cm (26 AWG), or any other suitable diameter. Secondary recharging coil 68 is coupled to the recharging feedthroughs 80 with an electrical connection 86. Electrical connection 86 is protected with a hermitic seal to prevent electrical connection 86 from being exposed to biological tissue or fluids. The hermetic seal is a biocompatible material and can take many forms including potting material, polymer encapsulation, coil cover with polymer seal, or the like.

The embodiment in FIG. 4A has secondary recharging coil 68 carried on the proximal face 76 of implantable medical device 20 with magnetic shield 70 positioned between secondary recharging coil 68 and proximal face 76. External secondary recharging coil 68 increases recharge efficiency because secondary recharging coil 68 is located just under the surface of the skin to decrease coupling distance, and magnetic shield 70 is position to both attract flux lines to the area of secondary recharging coil 68 and reduce flux lines from coupling into housing 66 to reduce eddy currents in housing 66. The embodiment in FIG. 4B has an internal secondary recharging coil 68 with magnetic shield 70 positioned between internal secondary recharging coil 68 and electronics 40. The internal secondary recharging coil 68 reduces manufacturing complexity and magnetic shield 70 improves coupling and reduces eddy currents induced into the electronics 70. The internal secondary recharging coil 68 should also allow for the greatest potential for heating of the housing 66 of the device 20 during recharging to aid in clearance of an infection in proximity to the device 20. The embodiment in FIG. 4C has a remote secondary recharging coil 68 located away from housing 66 with magnetic shield 70 positioned on distal side 84 of secondary recharging coil 68. Remote secondary recharging coil 68 permits the clinician more positioning options while magnetic shield 70 improves coupling. However, it will be understood that such remote secondary coils 68 may not allow for sufficient heating of housing 66 of device 20 to be useful to aid in clearing an infection in proximity to device 20. Additional information regarding recharging of implantable medical devices 20 is provided in U.S. Pat. No. 6,850,803, entitled "Implantable Medical Device With A Recharging Coil Magnetic Shield", and issued on Feb. 1, 2005.

Various configurations for sensor arrangement are also depicted in FIGS. 4A-C in block form. Sensors 50, 50' are coupled to electronics 40. While not shown in FIGS. 4B-C, feedthroughs and electrical connections are used as appropriate in the configurations shown. Sensors 50, 50' may be disposed in or on, generally in proximity to, device 20 or portion thereof. Sensor 50, 50' may be exposed to an external surface of device 20 to be in contact with body tissue or fluid when implanted in a patient, or may be contained in housing 66, as appropriate. If sensor 50, 50' is a temperature sensor for monitoring heating of device 20 or surrounding patient tissue during recharge, it may be desirable for sensor 50, 50' to be located in proximity to secondary coil 68 or near the surface of the device housing 66.

In FIG. 4A-C, one or two sensors 50, 50' are depicted, but it will be understood that any number of temperature or other sensors may be employed. In the embodiments, depicted in FIGS. 4A-C, sensor 50 is a temperature sensor and sensor 50' is a temperature sensor or other sensor. Sensor 50 is located generally in proximity to secondary coil 68 or in proximity to housing 66 and may serve to detect temperature during recharging of power source 58. Sensor 50 may also be used to monitor infection in proximity to device 20. In the embodiment depicted in FIG. 4C, sensor 50' may be a temperature sensor. The use of more than one temperature sensor at different locations may serve to improve the accuracy of determinations as to whether temperature at a given sensor location is indicative of infection by comparing the temperature at the given location to temperature at a location removed from the given location. Additional information regarding the use of temperature sensors at two locations for improved infection monitoring is described in U.S. patent application Ser. No. 11/737,171, entitled "Implantable Therapy Delivery System Having Multiple Temperature Sensors", filed on even date herewith, naming Martin Gerber and John Rondoni as inventors, and having P0028539.00 as an attorney docket number, which application is incorporated herein by reference in its entirety to the extent that it does not conflict with the disclosure presented herein. Of course sensor 50' may detect indicators of infection or physical or chemical stimuli other than temperature.

It will be understood that the components described in FIGS. 1-4 are but examples of components that an implantable device 20 may include and that many other device or system configurations may be employed to carry out the methods described below. However, for the sake of convenience, the discussion that follows with regard to the methods illustrated in the flow diagrams of FIGS. 5-9 will refer to components as described with regard to FIGS. 1-4.

Figure 5:
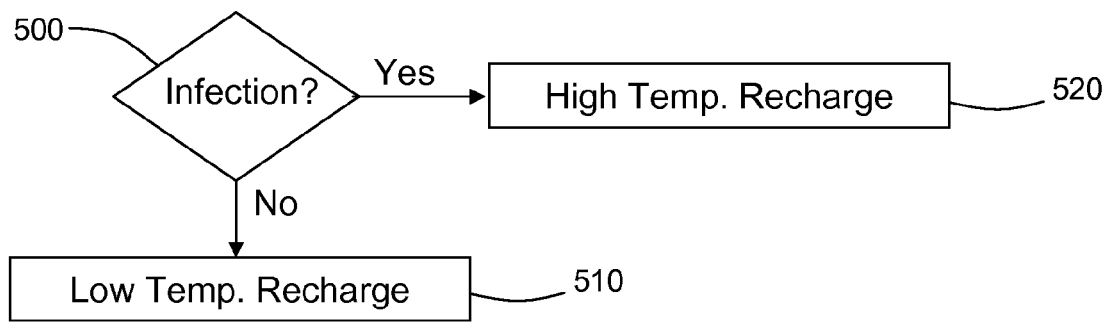
FIGS. 5-9 are flow diagram of representative methods.

Referring to FIG. 5, a flow diagram of an exemplary method is shown. According to various embodiments, the method includes transmitting energy capable of recharging an implantable device 20 from an external source to the implanted device 20. The method further includes determining whether an infection is present in proximity to an implantable rechargeable medical device 20 (500). Such a determination may be performed by processor 110 based on information received by one or more sensors 50, 50'. If it is determined that no infection is present in proximity to device 20, the transmitted energy will have a first parameter profile (510) that is designed to keep heating of the implanted device 20 below a temperature threshold ("Low Temperature Recharge"). If an infection is determined to be present in proximity to device 20, the transmitted energy will have a second parameter profile (520) that is designed to allow for heating of device 20 during recharging ("High Temperature Recharge"). Thus, the second energy parameter profile, relative to the first energy parameter profile, is configured to cause increased heating of the implanted device 20 during the transmission of the recharge energy. An energy parameter profile designed to cause increased heating may be achieved by increasing the amplitude or the frequency of the energy transmitted. Heat generated in the housing 66 (or the "can") of the implanted device 20 during a recharging process is due, at least in part, to the production of eddy currents in the can, which may be affected by changing, inter alia, the frequency or amplitude of the current applied to the primary coil in recharge head 30. The amplitude of the current is proportional to field strength. Generally, frequency will be in a range from 5 kHz to 100 kHZ, and field strength will be in a range from 1000 Amp/meter to 4000 Amp/meter. It will be understood that the material that forms the can may also have an impact on the formation of eddy currents and thus the amount of heat generated in the can. For example, eddy currents are more readily produced in grade 1 titanium than in grade 9 titanium.

Figure 6:
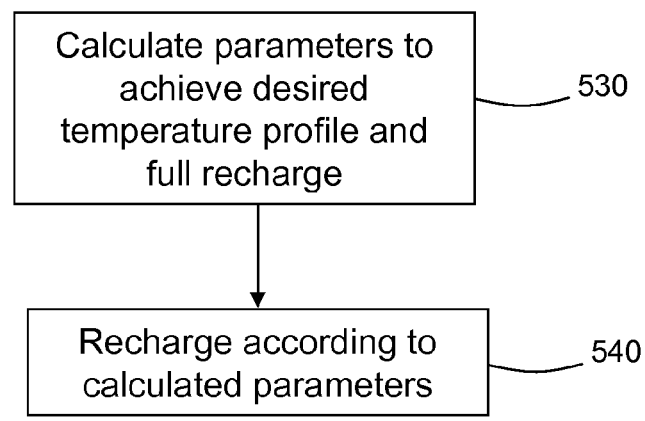

For example and referring to FIG. 6, the first and second energy parameters may be calculated to achieve a desired temperature profile and a full recharge (530) and recharging may be carried out according to the calculated parameters (540). According to various embodiments, recharger 28 may interrogate device 20 via telemetry to determine battery life remaining or energy requirements to achieve a full recharge of power source 58. Based on such information, the recharge energy parameters may be calculated to achieve a full recharge and a desired temperature profile. For example, the first energy parameter profile (relative to the second energy parameter profile) may result in more slow charging of power source 58 by transmission of lower amplitude current over a longer duration of time to achieve a full recharge, but not to exceed a temperature threshold in proximity to device 20. Similarly, the second energy parameter profile (relative to the first energy parameter profile) may result in more rapid charging of power source 58 by transmission of higher amplitude current over a shorter period of time to allow for additional heating of device 20. Such calculations may be based on models of heat production during recharge or using any other suitable algorithm. The determination as to battery life remaining, amount of energy required to achieve a full recharge, or parameters to achieve desired temperature profile and full recharge may be made by device 20, recharger 28, or a device in communication with either the implanted device 20 or recharger 28. Recharging (540) may occur with or without temperature monitoring. For example, current on the secondary coil 68 may be measured to provide an estimate of heating in the can, as current on the coil 68 is proportional to the strength of the magnetic field around the can, which is proportional to the eddy currents produced in the can. By way of another example, algorithms akin to those employed by some currently available rechargeable implantable medical device systems may be used. Such algorithms are currently employed to determine what energy parameter profile may be appropriate to achieve efficient recharge without excessive heating; and may take into account field strength, frequency, temperature at the surface of the skin (temperature sensor in recharge head 30), and current in battery. The input parameters may be refreshed periodically, e.g. every few seconds, to update the model.

Figure 7:
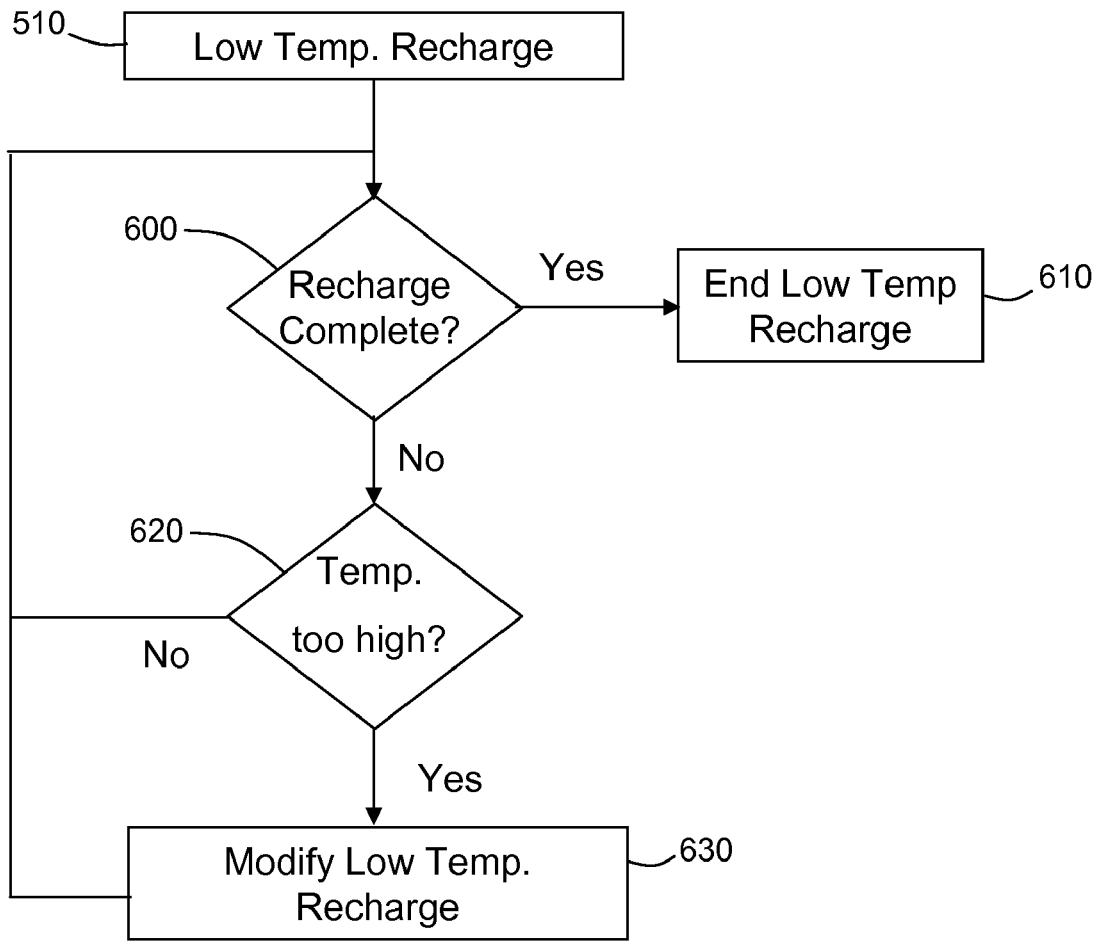
Figure 8:
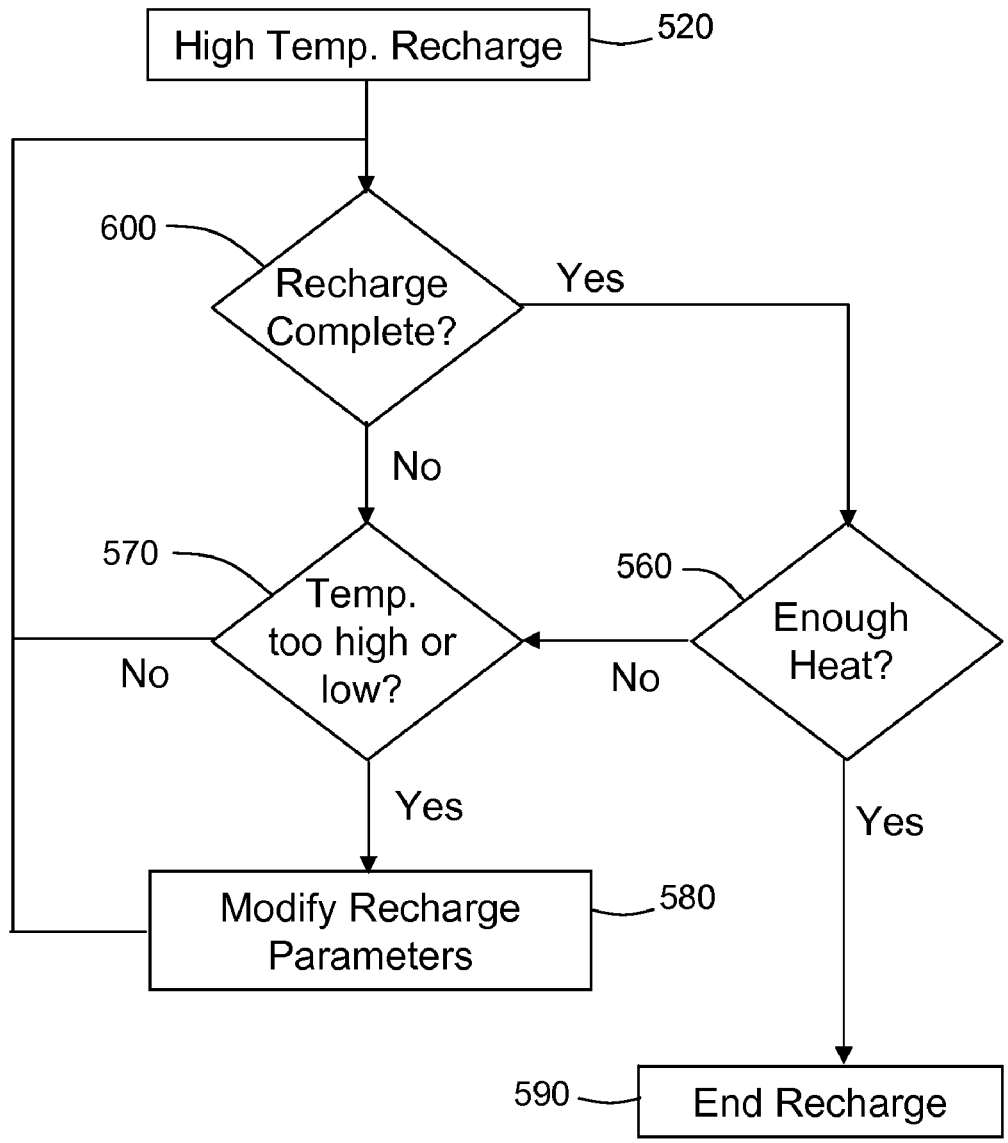
Figure 9:
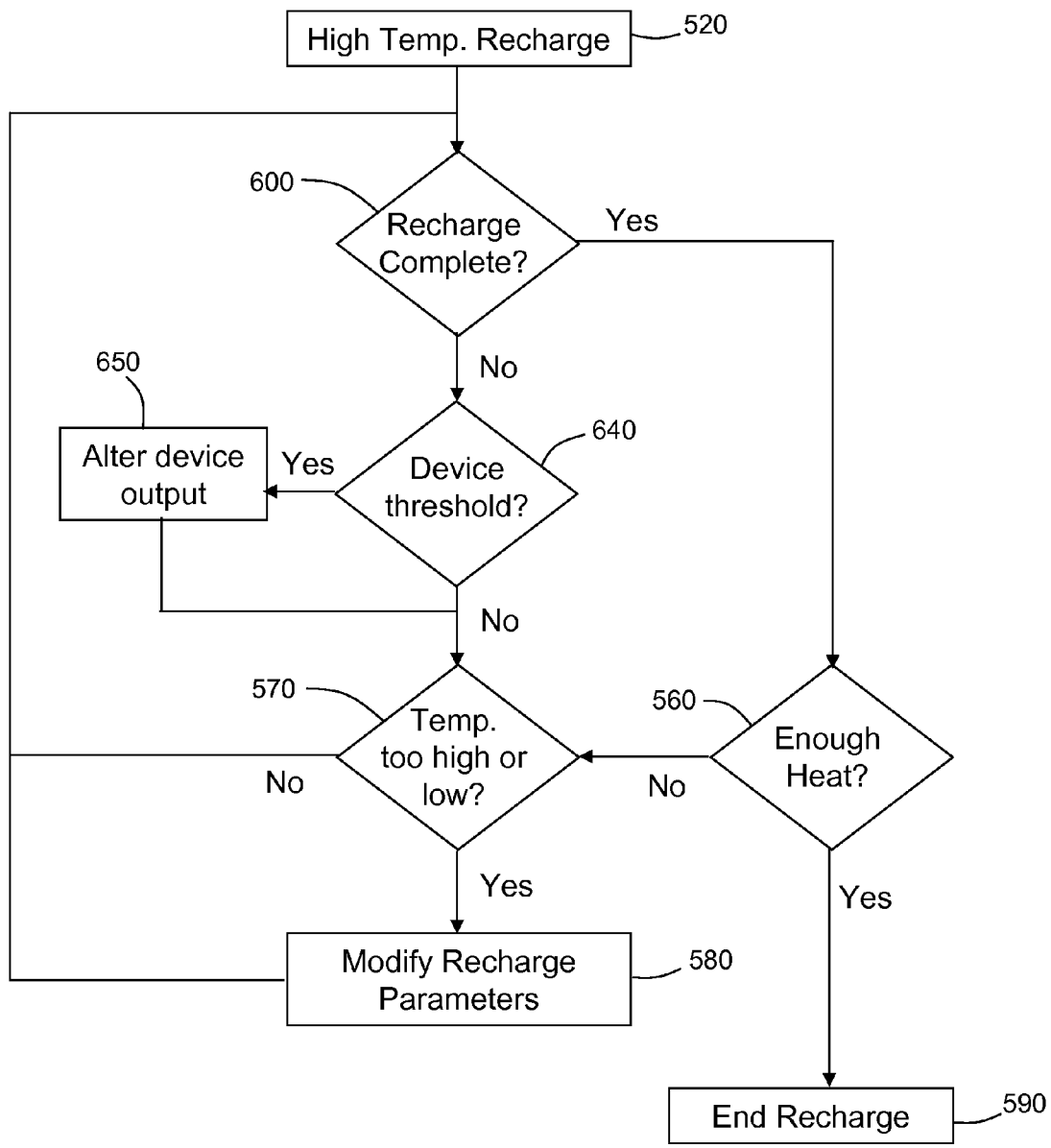

Examples of methods including transmission of recharge energy in combination with temperature monitoring are depicted in FIGS. 7-9. However, it will be understood that algorithms or estimates of temperature, e.g. as discussed above, may be substituted for monitoring of actual temperature. Referring first to FIG. 7, a flow diagram of a representative method for performing a low temperature recharge (510—see FIG. 5) is depicted. The method includes transmitting recharge energy having a first energy parameter profile (510), which may be calculated as above, from an external source (e.g., recharger 28) to implanted device 20. The method includes determining whether the recharge is complete (600). Such a determination may be made prior to transmission of the energy; e.g. the determination being already made in the calculation of the energy parameter profile. Alternatively, or in addition, such a determination (600) may be made through the use of information from power management module 160, recharge module 195, or other component of electronics 40 during transmission of the recharge energy. If the recharge is determined to be complete, energy transmission associated with the low energy recharge event may be ended (610). If the recharge is determined to be incomplete, a determination may be made as to whether a temperature threshold has been crossed (620). Such a determination may be made by processor 110 by comparing information obtained by temperature sensor 50, 50' and stored in memory 120 to threshold values stored in memory 120. If the temperature is determined not to be too high; e.g. the temperature threshold has not been crossed, the low temperature recharge (510) according to the initial first energy parameter profile may be continued to be applied. If the temperature is determined to be too high, the first energy parameter profile may be modified (630) such that recharging causes less heating of device 20, e.g. lowering of amplitude of delivered current or temporarily suspending transmission of recharge energy. By way of example, information regarding the temperature may be telemetrically transmitted from implanted device 20 to the external source (e.g., recharger 28) to signal external source to modify parameters. The recharge process may continue with the modified energy parameters.

Referring to FIG. 8, a flow diagram of a representative method for performing a high temperature recharge (520—see FIG. 5) is depicted. The method includes transmitting recharge energy having a second energy parameter profile (520), which may be calculated as above, from an external source (e.g., recharger 28) to implanted device 20. The method includes determining whether the recharge is complete (600). Such a determination may be made prior to transmission of the energy; e.g. the determination being already made in the calculation of the energy parameter profile. Alternatively, or in addition, such a determination (600) may be made through the use of information from power management module 160, recharge module 195, or other component of electronics 40 during transmission of the recharge energy. If the recharge is determined to be complete, a determination may be made as to whether the device has been sufficiently heated (560) for a desired therapeutic purpose. Such a determination may be made, for example, by processor 110 based on information received by one or more temperature sensors 50, 50'. For example, processor may compare a threshold heat value stored in memory to information stored in memory regarding temperature to make the determination (560). If it is determined that device 20 has been heated a desired amount, transmission of the recharge energy may be ended (590). If it is determined that device 20 has not been heated the desired amount (560) or if the recharge is determined to be incomplete (600), a determination may be made as to whether a temperature in proximity to the device is above or below a desired range (570). Such a determination may be made by processor 110 by comparing information obtained by temperature sensor 50, 50' and stored in memory 120 to temperature range values stored in memory 120. If the temperature is determined to be within the desired temperature range, the high temperature recharge (510) according to the initial second energy parameter profile may be continued to be applied. If the temperature is determined to be outside the desired temperature range, the second energy parameter profile may be modified (580) such that recharging the temperature in proximity of the device 20 to reside in the desired range, e.g. lowering of amplitude of delivered current or temporarily suspending transmission of recharge energy, or increasing amplitude of the delivered current, as appropriate. By way of example, information regarding the temperature may be telemetrically transmitted from implanted device 20 to the external source (e.g., recharger 28) to signal external source to modify parameters. The recharge process may continue with the modified energy parameters.

As shown in FIG. 9, the method depicted in FIG. 8 may further include determining whether a device threshold has been crossed (640) and altering device output (650) if the threshold is crossed. Such steps may be desirable when device 20 is an infusion device or other device, where increased temperatures may result in delivery of excess or inappropriate levels of therapy. For example, increased device temperature may result in excess delivery of therapeutic agent from an implantable infusion device. As such, device output may be altered based on monitored temperature in proximity to the device. For example, the rate of delivery of therapeutic agent may be appropriately lowered or altered, depending on the monitored temperature. In various embodiments, therapeutic output may be temporarily suspended until temperature in proximity to the device returns to an acceptable range.

An additional concern with implantable drug infusion devices is that increased temperatures may result in degradation of therapeutic agent to be delivered by the infusion device. One skilled in the art will be able to balance the desire for therapeutic heat for treatment of a condition associated with an implanted device and the potential adverse effects on the therapy and therapeutic agent to make a decision regarding what the device threshold may be on a case-by-case, therapy-by-therapy, or therapeutic agent-by-therapeutic agent basis. Such device thresholds or other thresholds, desired values or ranges as discussed herein, may be loaded into memory 120 by a physician in the clinic, by a manufacturer prior to shipment, or the like.

Low temperature recharging (510) or transmission of recharge energy having a first energy parameter profile may be configured to keep temperature in proximity to device 20 to within 2 C, or perhaps 1.5 C or 1 C, of a temperature prior to transmission of the low temperature recharge energy. The thresholds for temperature increases associated with such low temperature recharge energy may be kept conservatively low for purposes of patient safety.

However, detection of a condition such as infection in proximity of the device places the patient safety at risk and more aggressive heating may be warranted with high temperature recharging (520) or transmission of recharge energy having a second energy parameter profile. For example, it may be desirable for temperature at a surface of the implanted device to rise 2 C, 5 C, 7 C, 10 C or more from a temperature prior to transmission of the energy, perhaps for the majority of the time that the energy is transmitted. In some embodiments, it may be desirable to pulse heating. For example, it may be desirable to cause temperature at a surface of the implanted device to rise more than 2 C, 5 C, 7 C, or 10 C from a temperature prior to transmission of the energy, return to within 2 C, 5 C, 7 C, or 10 C of the temperature prior to transmission of the energy, and then rise more than 2 C, 5 C, 7 C, or 10 C from a temperature prior to transmission of the energy. In some embodiments, it may be desirable to cause tissue ablation in proximity of the device. The extent of tissue ablation may be controlled by the rate of the heating of the device caused by transmission of the energy according to the second energy profile. For example, a rapid quick rise in amplitude of current of transmitted energy, followed by a rapid quick decrease, may allow for ablation of a small amount of tissue. On the other hand, sustained elevated amplitude may result in greater tissue ablation. Generally, tissue ablation will occur with a temperature increase of 5 C to 10 C, depending on the amount of time device 20 is held at the increased temperature. Even higher temperature increases may be needed if the duration of the temperature increase is short. Ablation of tissue may be desirable in instances where tissue in proximity to the implanted rechargeable device is infected.

In various embodiments, the second energy parameter profile may be initially configured to generate significant heating of device 20. For example, a 100 kHz frequency and 4000 Amp/meter field strength may be applied to the primary coil in recharge head 30. The temperature may then be monitored and a prediction as to future temperature values may be made, e.g. based on the rate of temperature increase. If current or predicted future temperature crosses a threshold, the second energy parameter profile may be modified such that it is configured to generate less heating of device 20.

While the discussion above has focused primarily on the use of heat to treat an infection in proximity to an implantable medical device. It will be understood that many other conditions, such as pain or discomfort, edema, seroma, and hematoma, may benefit from the use of such heating. The principles disclosed herein may readily be applied to the treatment of such other conditions.

One of skill in the art will understand that components or steps described herein regarding a given embodiment or set of embodiments may readily be omitted, substituted, or added from, with, or to components or steps of other embodiments or sets of embodiments, as appropriate or desirable.

It will be further understood that a computer readable medium containing instructions that when implemented cause an implantable medical device (or system including an implantable medical device) to perform the methods described herein are contemplated. Devices and systems including the computer readable medium are also contemplated.

Patent applications directed to infection monitoring that may provide additional insight into the teachings provided herein include the following patent applications filed on even date herewith: (i) U.S. patent application Ser. No. 11/737,173, entitled "Infection Monitoring", naming Martin Gerber and John Rondoni as inventors, and having P0028125.00 as an attorney docket number, now abandoned; (ii) U.S. patent application Ser. No. 11/737,170, entitled "Infection Monitoring", naming Martin Gerber and John Rondoni as inventors, and having P0028529.00 as an attorney docket number; (iii) U.S. patent application Ser. No. 11/737,169, entitled "Event Triggered Infection Monitoring", naming Martin Gerber and John Rondoni as inventors, and having P0028528.00 as an attorney docket number; and (iv) U.S. patent application Ser. No. 11/737,176, entitled "Refined Infection Monitoring", naming Martin Gerber and John Rondoni as inventors, and having P0028541.00 as an attorney docket number. The above-referenced patent applications are hereby incorporated herein by reference in their respective entireties to the extent that they do not conflict with the disclosure presented herein.

Thus, embodiments of the CONTROLLING TEMPERATURE DURING RECHARGE FOR TREATMENT OF CONDITION are disclosed. One skilled in the art will appreciate that the present invention can be practiced with embodiments other than those disclosed. The disclosed embodiments are presented for purposes of illustration and not limitation, and the present invention is limited only by the claims that follow.

What is claimed is:

1. A method comprising:
    determining whether an infection is present in proximity to an implanted rechargeable medical device; and
    transmitting energy from an external source to the implanted device, the energy capable of recharging the implanted device,
    wherein the transmitted energy has a first parameter profile if it is determined that no infection is present in proximity to the implanted device, wherein the energy transmitted has a second parameter profile if it is determined that an infection is present in proximity to the implanted device, and wherein the second energy parameter profile, relative to the first energy parameter profile, is configured to cause increased heating of the implanted device during the transmission of energy.

2. The method of claim 1, wherein the second energy profile is configured to cause temperature at an external surface of the implanted device to rise 2 C or more from a temperature prior to transmission of the energy.

3. The method of claim 1, wherein the second energy profile is configured to cause temperature at an external surface of the implanted device to rise more than 2 C from a temperature prior to transmission of the energy, return to within 2 C of the temperature prior to transmission of the energy, and rise more than 2 C from a temperature prior to transmission of the energy.

4. The method of claim 1, wherein the second energy profile is configured to cause temperature at an external surface of the implanted device to rise more than 2 C from a temperature prior to transmission of the energy for the majority of the time that the energy is being transmitted.

5. The method of claim 1, wherein the second energy profile is configured to cause tissue ablation in proximity of the device.

6. The method of claim 5, wherein the extent of tissue ablation is controlled by the rate of the heating of the device caused by transmission of the energy according to the second energy profile.

7. The method of claim 1, wherein determining whether an infection is present in proximity to the implanted device is performed by the implanted device.

8. The method of claim 1, further comprising calculating the amount of energy needed to recharge the device and calculating the first or second energy profile based the amount of energy needed to recharge the device.

9. The method of claim 8, wherein calculating the amount of energy needed to recharge the device is preformed by a device operably coupled to the external source.

10. The method of claim 1 further comprising monitoring temperature in proximity to the device during the transmission of energy and determining whether the monitored temperature is within a desired temperature range.

11. The method of claim 10, further comprising modifying one or more parameters of the transmitted energy if it is determined that the monitored temperature is not within the desired temperature range.

12. The method of claim 10, further comprising transmitting information regarding the monitoring temperature to the device and transmitting a signal from the implanted device to the external source if it is determined that the monitored temperature is not within the desired temperature range.

13. The method of claim 1, wherein determining whether an infection is present in proximity to the implanted rechargeable medical device comprises monitoring an indicator of infection in proximity to the implanted medical device.

14. The method of claim 13, wherein monitoring the indicator of infection comprises monitoring temperature.

15. The method of claim 14, wherein monitoring temperature comprises monitoring temperature detected by a temperature sensor.

16. The method of claim 15, further comprising monitoring temperature in proximity to the device during the transmission of energy, wherein monitoring temperature in proximity to the implanted device during the transmission of the energy comprises monitoring temperature detected by the temperature sensor.

17. A method comprising:
transmitting energy from an external source to an implanted rechargeable device, the energy being capable of heating an external surface of the implanted device and being capable of recharging the implanted device;
monitoring temperature in proximity to the device during the transmission of the energy;
determining whether the monitored temperature is above or below a desired temperature range;
modifying one or more parameters of the transmitted energy if it is determined that the monitored temperature is above or below the desired temperature range, the modified parameters being configured to cause the monitored temperature to reside within the desired temperature range;
determining whether the implanted device is recharged to a desired level;
determining whether the device has been heated a desired amount; and
stopping the transmission of energy if it is determined that the device is recharged to the desired level and if the device has been heated the desired amount.

18. The method of claim 17, wherein the transmitted energy is configured to cause temperature at the surface of the implanted device to rise 2 C or more from a temperature prior to transmission of the energy.

19. The method of claim 17, further comprising determining whether the monitored temperature exceeds a threshold and altering therapeutic output from the implantable medical device if the threshold is exceeded.

20. A system comprising an implantable rechargeable medical device and an external device comprising an external source, the system further comprising:
means for determining whether an infection is present in proximity to the implanted rechargeable medical device; and
means for transmitting energy having a first or second energy parameter profile from the external source to the implanted device, the energy capable of recharging the implanted device,
wherein the transmitted energy has the first parameter profile if it is determined that no infection is present in proximity to the implanted device,
wherein the energy transmitted has the second parameter profile if it is determined that an infection is present in proximity to the implanted device, and
wherein the second energy profile, relative to the first energy profile, is configured to cause increased heating of the implanted device during the transmission of energy.

21. A system comprising:
means for transmitting energy from an external source to an implanted rechargeable device, the energy being capable of heating a surface of the implanted device and being capable of recharging the implanted device;
means for monitoring temperature in proximity to the device during the transmission of the energy;
means for determining whether the monitored temperature is above or below a desired temperature range;

means for modifying one or more parameters of the transmitted energy if it is determined that the monitored temperature is above or below the desired temperature range, the modified parameters being configured to cause the monitored temperature to reside within the desired temperature range;

means for determining whether the implanted device is recharged to a desired level;

means for determining whether the device has been heated a desired amount; and means for stopping the transmission of energy if it is determined that the device is recharged to the desired level and if the device has been heated the desired amount.

* * * * *